United States Patent [19]

Krohn et al.

[11] 4,003,991
[45] Jan. 18, 1977

[54] OPHTHALMIC FORMULATION

[75] Inventors: David L. Krohn, New York, N.Y.; Samuel H. Ronel, Princeton, N.J.

[73] Assignee: National Patent Development Corporation, New York, N.Y.

[22] Filed: Aug. 27, 1974

[21] Appl. No.: 501,117

[52] U.S. Cl. .................................. 424/81; 424/78; 424/271; 424/273
[51] Int. Cl.² ................. A61K 31/74; A61K 31/78; A61K 31/415
[58] Field of Search ............... 424/273, 78, 81, 19, 424/32

[56] References Cited

UNITED STATES PATENTS

| | | | |
|---|---|---|---|
| 3,863,633 | 2/1975 | Ryde et al. | 424/78 |
| 3,868,445 | 2/1975 | Ryde et al. | 424/19 |
| 3,907,985 | 9/1975 | Rankin | 424/78 |

*Primary Examiner*—Sam Rosen
*Attorney, Agent, or Firm*—Cushman, Darby & Cushman

[57] ABSTRACT

An ophthalmic "ointment" comprising water, a solid water-soluble polymer of controlled molecular weight, and a medicament or therapeutic agent such as pilocarpine in its pharmacologically acceptable salts.

34 Claims, No Drawings

OPHTHALMIC FORMULATION

The present invention relates to viscous homogeneous mixtures (hereinafter, for convenience, termed "ointment") comprising a medicament and relatively high concentrations of solid, water-soluble polymers dissolved in an aqueous medium.

In the past many medicaments or therapeutic agents have long been topically administered for the treatment of various eye disorders. Pilocarpine has proven especially effective for the control of glaucoma. However, the effect of aqueous solutions of pilocarpine have been limited by (i) an apparent resistance into the interior eye, and (ii) by the relatively short duration on the corneal surface of effective drug concentration because of both tear dilution and "washing out" effect. Prior investigators also have shown that pilocarpine penetrates the eye through the cornea and not through the conjunctiva-scelera.

The mechanism of transcorneal pilocarpine flux appears to be carrier-mediated. Excessive doses of pilocarpine which occur in typical pilocarpine therapy overload the carrier mechanism and consequently, substantial amounts of pilocarpine are trapped in the cornea with a resultant apparent low flow efficiency. Explained differently, the cornea will accept relatively large amounts of pilocarpine but is unable to transport it further. The fate of the entrapped pilocarpine is unknown but it is believed to be detoxified and denatured in some manner.

The resistance of the cornea to passage of pilocarpine from the surface into the internal eye has been documented by in vitro studies (Krohn and Breitfeller, Investigative Ophthalmology, Vol. 13, pages 312–316, 1974). These studies have shown that transcorneal flux of the drug is scanty under ordinary drop therapy conditions. These studies also demonstrated that under conditions simulating normal physiology, tear flow has removed all available pilocarpine from the corneal surface within ten minutes of application. Of the total amount of pilocarpine administered in drop form, only 0.16% is found in the analog of the internal eye.

In addition, over and above the limitations of pilocarpine corneal penetration in ordinary aqueous drops, there appears to be a striking resistance of the tissue effective (in controlling glaucoma) within the eye to penetration of this drug, even when it has succeeded in entering the internal eye. This phenomenon has been reported by Tornqvist (Investigative Ophthalmology Vol. 3, page 388, 1964). Further confirmation has been reported by Lyons and Krohn (American Journal of Ophthalmology, Vol. 75, page 885, 1973) of this resistance, and evidence has been presented suggesting that pigmented tissue of the ciliary body may be in part responsible for this "sentinel" effect. To overcome this resistance, it appears that the effector tissue in glaucoma control must be saturated or "overwhelmed" before pilocarpine can be effective in resistant eyes.

The striking effect of hydrogel lenses "soaked" with pilocarpine, i.e., sparingly cross-linked hydrophilic polymers or hydrogels in the form of a soft plastic lens and "soaked" with pilocarpine in overcoming both corneal and intra-ocular areas of resistance and in enhancing pilocarpine control of glaucoma in resistant cases is well documented in the ophthalmic literature. "Lenses" used for such therapeusis suffer from several disadvantages inasmuch as the patient must be fitted with these "lenses" and properly fitted "lenses" compatible with the patient's refractive error may be required for full therapeutic use. Furthermore, a certain amount of training is required to enable the patient to place and remove the "lenses". These factors severely limit the use of pilocarpine-soaked "soft plastic" lenses in glaucoma therapy.

There have been proposals in the past to use high molecular weight polymers such as hydroxypropyl methyl cellulose, polyvinyl alcohol, hydroxyethylcellulose and the like in relatively small concentration, e.g., below 5 weight percent, with aqueous pilocarpine solutions in an endeavor to increase the efficacy of aqueous pilocarpine penetration into the anterior chamber and improvement has been noted for up to 15 hours. It has also been proposed to employ aqueous pilocarpine solutions containing polyethylene oxide of very high molecular weight (at least about 100,000 and preferably of the order of 4,000,000, see U.S. Pat. No. 3,767,788) in an amount up to 2 weight percent. Optionally, there can be present polyvinyl-pyrrolidone (PVP) of unspecified molecular weight in an amount of 0.5 to 10%. The PVP is stated to act as a detoxicant, anti-toxin binder, to protect the solution from breakdown due to particle agglomeration, to act as a demulcent lubricant, and to prevent involuntary eyelid contraction.

Accordingly, it is an object of the invention to provide as improved system for transporting a therapeutic agent such as pilocarpine in its pharmacologically compatible salts to the internal eye.

Another object is to provide a novel system which will provide drug therapy to the external ocular tissues as well as the tissues in the internal eye, the latter by virtue of enhanced penetration afforded by prolonged surface contact of said system with said external ocular tissues.

These and other objects can be achieved by preparing a novel viscous, homogeneous mixture (ointment) comprising a medicament or active therapeutic agent such as pilocarpine in its pharmacologically acceptable salt and relatively high concentrations of solid, water-soluble polymers (described hereinafter) dissolved in an aqueous medium.

The essential requirement of "pulsing" or enhanced transcorneal pilocarpine penetration is long continued contact of the effective drug molecules with the surface of the cornea. This can be achieved by the use of "soft plastic" lenses. By the practice of suitable embodiments of the invention, the use of the novel ophthalmic ointments, such as those containing pilocarpine as the medicament, allows an enhanced "pulsing" of the pilocarpine into the internal eye through a resistant cornea with an ease of administration not afforded by the pilocarpine-soaked "soft plastic" lenses.

It has been noted that resistance to corneal penetration of various drugs administered topically will vary depending on the characteristics, e.g., molecular structure, of the candidate drug. It has been observed, however, that transcorneal penetration is decidedly increased by the prolonged surface contact afforded through the use of the novel ophthalmic ointment. It is believed that the function of the critically defined solid, water-soluble polymer component in the novel ointment is to saturate the putative "carrier mechanism" but not to overload it. This is indicated by an absence of a corneal "depot" or "reservoir" phenomena when using the novel ointments. This is in contrast to the striking "depot" effect which results from ordinary simulated drop therapy, e.g., loss of about 30 percent of administered drug loss into corneal tissue.

The medicaments or active therapeutic agents which can be employed in the practice of the invention include, by way of illustrations, the corticosteroids such as hydrocortisone acetate, prednisolone acetate, and dexamethasone; antibiotics such as neomycin, bacitracin, and the penicillins; the soluble sulfonamides including sulfacetamide; other commonly required drugs such as, scopolamine hydrobromide, epinephrine bitrartrate, phenylephrine HCl, prostigmin bromide, idoxuridine, phospholine iodide, pilocarpine in its pharmacologically acceptable salts, especially the hydrochloride or the nitrate.

The concentration of the medicament in the novel formulation can vary over a wide range depending on the medicament of choice, the solid water-soluble polymers of choice, the disease to be treated, the clinically observed rate of elution, and other considerations. In general, at least a therapeutically effective amount is used which amount is within established concentration ranges of safety and efficacy. Thus, the novel ointments can contain the medicament such as a pilocarpine salt in varying concentrations, e.g., from 0.1 weight percent to its maximum solubility in an aqueous medium. For pilocarpine hydrochloride, the maximum solubility value has been found to be about 16 weight percent. A useful concentration range for pilocarpine salts is from about 2 to about 16 weight percent and preferably from about 3 to about 12 weight percent, based on the novel ointment. Depending on the factors illustrated above, the concentration of other medicaments would vary within established levels of safety, efficacy, and effectiveness. For steriods such as dexamethasone a useful concentration range is from about 0.1 to about 1 weight percent whereas it is quite desirable to use from about 1 to about 5 weight percent of the 1-epinephrine derivatives, based on the weight of the novel ointment.

The polymers which are an essential component in the invention are normally-solid materials which have well-defined average molecular weights ranging from about 15,000 to about 500,000. In the practice of preferred embodiments of the invention novel ointments comprising polymers having average molecular weights in the range of from about 25,000 to about 250,000 optimize the advantages discussed herein. The polymers are water-soluble in acidic and basic media, e.g., pH of from 4 to about 8. They are compatible with the medicament such as pilocarpine (as the free base or its salt such as the hydrochloride or nitrate salts).

An amount of solid, compatible, non-toxic, water-soluble polymer is employed in the novel ointment which, in preferred embodiments of the invention, is sufficient to impart to such ointment a slow-flow characteristic which is substantially shape-retaining as it (ointment) is forced from the opening of a tube (such as a smaller version of an ordinary tube of toothpaste) under mild hand squeezing of the tube. Such preferred ointments are soft and easily deformed under mild pressure, as by the pressure resulting from a blink of the eye. The viscosity of the novel ointment, as determined by Brookfield Viscomiter LVT, Spindle No. 3, Speed 12 rpm, at 25° C., can vary over a wide range, e.g., from a few hundred centipoises and upwards to 50,000, and even higher. In general, a maximum viscosity of about 25,000 centipoises should be sufficient for most purposes. A lower viscosity limit which is suitable is about 2000 centipoises. The concentration of the solid, water-soluble polymer component can be up to about 35 weight percent, and even higher, based on the total weight of the ointment. In general, a sufficient amount of polymer is employed to result in an ointment having the desired viscosity, for example, an ointment containing from 12 to 30 weight percent polymer.

The novel ointments, as indicated previously, are viscous, homogeneous formulations comprising water, polymer, and medicament. They are not "greasy" like petrolatum. They are non-toxic and non-irritating to the cornea and mucosa tissue. Unlike petrolatum-based medications, the novel ointments initially act after the first blink similarly to a plano-hydrogel lens. Upon tear dilution the ointments increasingly resemble tears. They provide decidedly increased transcorneal penetration because of the prolonged surface contact of the novel ointment with the corneal epithelium. This prolonged intimate contact of the medicament with the corneal epithelium appears to result in a high constant load of medicament for transport. The delivery system (novel ointment) apparently limits the load on the intracorneal "carrier mechanism" to the capacity of the carrier. This allows maximum transcorneal flux without loss to the intracorneal depot effect which is observed in drop therapy. Although this appears to be an explanation for the transport enhancement, the invention is not to be limited by the foregoing statements. In this respect the novel ointments are somewhat similar to "soft plastic" lenses since the concentration of the active ingredient is kept at a high level for a longer period of time, allowing an initial prolonged higher pulse (ability of the drug to get past the corneal resistance).

The high concentration of polymer component in the novel formulation is not used to thicken the formulation but rather to retain the medicament, e.g., pilocarpine salt, in a manner which is similar to retention of medicament in a "soft plastic" contact lens (see for example, Sedlacek, Cs. Oftalmologie, Vol. 21, pages 509–512 (1965) and Van Hoose, Investigative Ophthmalogy, May 1974, pages 377–383) or in an ocusert (see for example Ness U.S. Pat. No 3,618,604; Zaffaroni U.S. Pat. No. 3,626,940, or Higuchi U.S. Pat. No. 3,630,200) without the attendant disadvantages of inserting a foreign object into the eye. The present ointments are also considerably less costly and easier to apply than either contact lenses or ocular inserts.

The polymers which are suitable in the practice of the invention include the solid-water-soluble acrylic polymers, aliphatic amide polymers, and ethyleneimine polymers. Particularly suitable polymers are those characterized by the recurring unit

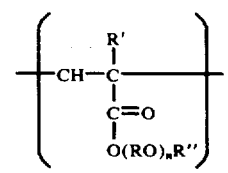

wherein R is a divalent aliphatic radical of 2 to 8 carbon atoms, preferably alkylene of 2 to 4 carbon atoms, and preferably still ethylene; wherein R' is hydrogen or alkyl of 1 to 4 carbon atoms, preferably methyl; wherein R" is hydrogen or alkyl of 1 to 12 carbon atoms, preferably hydrogen or alkyl of 1 to 4, and preferably still hydrogen; and wherein n is an integer of at least 1, e.g., 1 to 6, preferably one. A preferred class of solid polymers are characterized by at least about 20 weight percent, desirably at least 50 weight percent, preferably at least 80 weight percent of recurring Unit I supra. Any remaining units may be polymerized comonomers which are necessary to render said polymer water-soluble. Other vinyl comonomers can be chemically combined in the polymer as will be amply illustrated hereinafter. A preferred group of polymers are those which are characterized by about 50 to 98 weight percent of Unit I.

Illustrative polymers include the solid, water-soluble polymers of the hydroxyalkyl acrylates and the hydroxyalkyl methacrylates such as hydroxyethyl acrylate, hydroxypropyl methacrylate, hydroxypropyl acrylate, hydroxyethyl methacrylate, etc.; of the hydroxy lower alkoxy lower alkyl acrylates and methacrylates, e.g., diethylene glycol monoacrylate, diethylene glycol monomethacrylate, dipropylene glycol monoacrylate, dipropylene glycol monomethacrylate; of the lower alkoxyethyl acrylates and methacrylate, e.g., methoxyethyl acrylate, methoxyethyl methacrylate, ethoxyethyl acrylate and ethoxyethyl methacrylate; of triethylene glycol acrylate; of triethylene glycol methacrylate; of glycerol monoacrylate; of glycerol monomethacrylate; of methoxytriethylene glycol methacrylate; of methoxytriethylene glycol acrylate; of methoxytripropylene glycol methacrylate; of methoxytripropylene glycol acrylate; of methoxytrimethylene glycol methacrylate; of methoxytetraethylene glycol acrylate; of methoxy tetraethylene glycol methacrylate; of methoxypentaethylene glycol acrylate; of methoxypentaethylene glycol methacrylate; of methoxypentaethylene glycol acrylate; of methoxypentaethylene glycol methacrylate; of methoxyhexaethylene glycol acrylate; of methoxyhexaethylene glycol methacrylate; of methoxyheptaethylene glycol acrylate; of methoxyheptaethylene glycol methacrylate; of methoxytetrapropylene glycol acrylate; of methoxytetrapropylene glycol methacrylate; of methoxy pentapropylene glycol acrylate; of methoxypentapropylene glycol methacrylate; of methoxyheptapropylene glycol methacrylate, of ethoxytriethylene glycol acrylate; of ethoxytriethylene glycol methacrylate; of ethoxytetraethylene glycol acrylate; of ethoxytetraethylene glycol methacrylate; of ethoxytetrapropylene glycol methacrylate; of ethoxytetrapropylene glycol acrylate; of ethoxypentaethylene glycol methacrylate; of propoxytriethylene glycol acrylate; of propoxytriethylene glycol methacrylate; of butoxytriethylene glycol acrylate; of butoxytriethylene glycol methacrylate; of butoxytetraethylene glycol acrylate; of butoxytetraethylene glycol methacrylate; of butoxyhexaethylene glycol acrylate; of butoxytripropylene glycol methacrylate; of amyloxytriethylene glycol acrylate; of amyloxytriethylene glycol methacrylate; of amyloxytripropylene glycol acrylate; of hexoxytriethylene glycol acrylate; of hexoxytriethylene glycol methacrylate.

Highly desirable polymers are those which contain a sufficient amount of a water-solubilizing comonomer chemically combined therein in order to impart to the polymer a water-solubility characteristic. It is not necessary for the polymer to have been prepared from a monomeric mixture comprising the water-solubilizing comonomer if the omission of such comonomer would still result in a water-soluble polymer, e.g., the poly(2-alkenamides) as illustrated by water-soluble polyacrylamide. Within the broad scope of the invention the choice of the polymeric component in the novel formulation will be governed, to a significant degree, by its water-solubility characteristic (and other factors explained herein).

A particularly suitable class of polymers are those which contain a water-solubilizing comonomer polymerized therein in an amount which is sufficient to impart a virtually complete water-solubility characteristic to said polymers. Polymers which contain from about 2 and upwards to about 50 weight percent of water-solubilizing comonomer, more suitably about 5 to about 20 weight percent, are satisfactory in the practice of the invention.

A wide variety of solubilizing comonomers can be employed including (1) an alkali metal, e.g., sodium or potassium, salt of a polymerizable ethylenically unsaturated (or non-benzenoid unsaturated) organic acid, or (2) a strong acid salt of a polymerizable ethylenically unsaturated (or non-benzenoid unsaturated) amino containing monomer.

Examples of organic acids for making the alkali metal salts include acrylic acid, methacrylic acid, maleic acid, fumaric acid, itaconic acid, aconitic acid, cinnamic acid, crotonic acid, cyclohexenecarboxylic acid, propionic acid, mesaconic acid, citraconic acid, vinylsulfonic acid, p-vinyl-benzenesulfonic acid, partial esters such as mono-2-hydroxyethyl citraconate, mono-2-hydroxypropyl itaconate, mono-2-hydroxyethyl itaconate, mono-2-hydroxypropyl citraconate, mono-2-hydroxyethyl maleate, mono-2-hydroxypropyl fumarate, monomethyl itaconate, monoethyl itaconate, methyl Cellosolve itaconate (methyl Cellosolve is the monomethyl ether of diethylene glycol), methyl Cellosolve maleate, mono-2-hydroxyethyl aconitate.

Examples of strong acid salts of polymerizable amino containing monomers are the hydrochloric acid, hydrobromic acid, sulfuric acid, nitric acid, phosphoric acid, benzenesulfonic acid, naphthalenesulfonic acid, trichloroacetic acid, and p-toluene sulfonic acid salts of diethylaminoethyl methacrylate, of dimethyl aminoethyl methacrylate, of monomethylaminoethyl methacrylate, of t-butylaminoethyl methacrylate, of p-aminostyrene, of o-aminostyrene, of 2-amino-4-vinyl-toluene, of diethylaminoethyl acrylate, of dimethylaminoethyl acrylate, of t-butylaminoethyl acrylate, of piperidinoethyl acrylate, of piperidinoethyl methacrylate, of morpholinoethyl acrylate, of morpholinoethyl methacrylate, of 2-vinylpyridine, of 3-vinylpyridine, of 4-vinylpyridine, of 2-ethyl-5-vinylpyridine, of dimethylaminopropyl acrylate, of dimethylamino propyl methacrylate, of dipropylaminoethyl acrylate, of dimethylaminoethyl vinyl ether, of dimethylaminoethyl vinyl sulfide, of diethylaminoethyl vinyl ether, of aminoethyl vinyl ether, of 2-pyrolidionethyl methacrylate, of 3-(dimethylaminoethyl)-2-hydroxypropyl acrylate, of 3-(dimethylaminoethyl)-2-hydroxypropyl methacrylate, and of 2-aminomethyl acrylate, 2-aminoethyl methacrylate.

Other suitable water-solubilizing comonomers include acrylamide, methacrylamide, N-methylacrylamide, N-methylmethacrylamide, N-ethylacrylamide, N-ethylmethacrylamide, N-propylacrylamide, N-propylmethacrylamide, N-isopropylacrylamide, N-isopropyl methacrylamide, N-(2-hydroxyethylacrylamide), N-(2-hydroxyethyl methacrylamide), N,N-dimethylacrylamide, diacetone acrylamide, diacetone methacrylamide, and N-vinylpyrrolidone.

There also can be present amounts of other copolymerizable materials providing that they are not used in an amount sufficient to interfere with water solubility characteristics of the resulting polymer. Thus, there can be present as comonomers, for example, lower alkyl acrylates and methacrylate, in amounts up to 50 weight percent, e.g., methyl acrylate, ethyl acrylate, propyl acrylate, isopropyl acrylate, butyl acrylate, methyl methacrylate, ethyl methacrylate, isopropyl methacrylate and butyl methacrylate.

Mixtures of all of the foregoing illustrative monomers can be employed.

Additionally, solid water-soluble polymers of aliphatic amides can be used as the polymeric component in the novel ointment. Illustrative polymers include the water-soluble poly(2-alkenamides), e.g., polyacrylamide, poly(N-methylacrylamide), poly(2-propenamide), poly(2-butenamide), and the like; the water soluble polymers of 2-alkenamides and the monomers illustrated previously with/without the water-solubilizing comonomers; and the like.

Also less preferably there can be employed solid water soluble ethyleneimine homopolymers and copolymers as well as the sodium salt of sucrose acrylate polymer having free acrylic acid groups, e.g., Carpobol 940.

While not essential to the novel formulation there can be incorporated therein small amounts of polymers of vinylpyrrolidone such as polyvinylpyrrolidone, 85 vinylpyrrolidone/15 vinyl acetate copolymer, 94 vinylpyrrolidone/6 vinyl stearate, and the like, to impart to such formulation its recognized function. The polyvinylpyrrolidone and vinyl pyrrolidone copolymers can have molecular weights of 300 to 70,000 or more, and K values of 10 to 200, usually 15 to 100, as pointed out in Robinson U.S. Pat. No. 2,941,980, the entire disclosure of which is hereby incorporated by reference.

Likewise while not essential, there can be added water-soluble polar compounds including glycols such as ethylene glycol, trimethylene glycol, butanediol-1,3, butanediol-1,4, hexanediol-2,5, 2-methyl-2,4-pentanediol, heptanediol-2,4, 2-ethyl-1,3-hexanediol, diethylene glycol, triethylene glycol, tetraethylene glycols, and higher polyethylene glycols having a molecular weight up to 2000, and higher, desirably up to 800, e.g., hydroxyl terminated polymers of ethylene oxide having average molecular weights of 200–800; the polyoxyethyleneoxypropylene polyols especially glycols having molecular weights up to about 1500, desirably up to about 800; tri(hydroxyethyl) citrate; ethylene glycol monomethyl ether; ethylene glycol monoethyl ether; glyceryl triacetate; liquid sorbitol ethylene oxide adducts, ethylene glycol diacetate; providing the foregoing compounds do not adversely affect the eye.

Unless otherwise indicated throughout the specification and claims, all parts and percentages are by weight.

Examples 1–2 below illustrate the formation of water soluble copolymers.

EXAMPLE 1

To a 30-gallon reactor there was charged 40 lbs of hydroxyethyl methacrylate, 4 lbs of methacrylic acid, 120 obs of methanol and 0.05 lb of t-butyl peroctoate. The reactor was heated to 80° C. and allowed to stir for 6 hours to effect polymerization. To the polymer solution thus obtained was added 2.5 lbs. of sodium methoxide dissolved in 25 lbs. of methanol. The resulting solution was added slowly to a 10-fold excess of acetone to precipitate the polymer. After drying, a yield of 36 lbs. of water soluble polymer was obtained.

EXAMPLE 2

To a 30-gallon reactor there was charged 40 lbs. of hydroxyethyl methacrylate, 3 lbs. of dimethylaminoethyl methacrylate, 120 lbs. of methanol, and 0.05 lb. of diisopropyl percarbonate. The reactor was heated to 75° C. and was stirred 7 hours to effect polymerization. The polymer was isolated by precipitation with water, and dried. A yield of 35 lbs. was obtained. 10 Grams of the polymer was dissolved in 90 g. of 0.1 N HCl and the pH was adjusted to 4.5 with dilute sodium hydroxide.

EXAMPLE 3

A 20 weight percent solution was made by dissolving the copolymer of Example 1 (approximate average molecular weight of 75,000) in water at 22° C. to form a solution having a viscosity of 800 cps. Dissolution of said copolymer in water pH 7.4) was effected in about 24 hours. (This can be hastened with a magnetic spinner). Pilocarpine hydrochloride was added in an amount so as to provide a concentration of 4% pilocarpine and the admixture drawn into a 100 ml. pipette. Delivery was made onto a corneal button in a double chamber system. This system is described in Krohn, Investigative Ophthalmology, Vol. 13, No. 4, pages 312–316 (1974). Much of the admixture stuck to the pipette. In order to quantitate the delivery, the pipette was then eluted until free of the preparation and the pilocarpine hydrochloride analyzed in the elution fluid. This amount was subtracted from the total pilocarpine hydrochloride originally drawn into the pipette to determine dose. Three determinations were made:

| Time Exposure | Pilo Delivered | Pilo "tears" | Pilo Transported |
| --- | --- | --- | --- |
| 30 min | 2920 $\mu$g | 1940 $\mu$g | 8.40 $\mu$g |
| 30 min. | 2825 $\mu$g | 1775 $\mu$g | 6.78 $\mu$g |
| 120 min. | 3145 $\mu$g | 3070 $\mu$g | 11.12 $\mu$g |

The results suggest that in the short period — 30 minutes — the ointment may be even more effective than hydroxyethyl methacrylate polymer contact lens buttons (Soflens) since the delivered total pilocarpine hydrochloride is in the same range. Since the ointment is more vulnerable to the elution by the tear analog than is the lens, transport at 120 minutes is somewhat less than effected by the soaked lens. If "pulsing" as contrasted with constant flow effect is of major importance, the ointment might be actually more effective than the lens in glaucome control in resistant patients. It causes no change in the appearance of the cornea and appears to cause no distress or clouding when placed in the eye of a rabbit. It does not clog the small caliber plastic tubes of the constant flow pump system used for the tear flow analog in the double chamber model. It appears from the data obtained at 30 minutes and 120 minutes, the same approximate hydrochloride dose in (i) drops, (ii) contact lens, and (iii) novel ointment yields the following:

|  | 30 minutes | 120 minutes |
|---|---|---|
| drops | 2 µg | 4 µg |
| contact lens | 5 µg | 25 µg |
| novel "ointment" | 7.5 µg | 11 µg |

In addition, there is the question of whether there is some special quality in the ointment -cornea interface which decreases epithelial resistance to penetration which enhances flux beyond constant flow. In order to get some insight into both these problems, there were carried out another series of experiments to quantitate the transcorneal flux in the closed system when the pilocarpine hydrochloride was delivered simply in the tear analog constant flow without the lens or ointment. The tear flow delivery tube was arranged in all cases to be so close to the corneal vault apex that the tear flow was a continuum between the tip of the tube and the vault — that is, there was no dropping of the flow through air to avoid the potential problem of mechanical trauma from the dropping of fluid on the cornea. In these experiments, the concentration of the delivered pilocarpine hydrochloride was varied but the time interval held constant at 90 minutes. The total pilocarpine dose was estimated by the known and controlled flow at 1 ml/hr. Since this is subject to possible slight variation, the total dose, since it was not directly measured, is designated as "approximate". The following table shows the results:

Transcorneal Pilocarpine Hydrochloride Flux with Constant Flow Delivery, 90 Minutes

| Pilo conc. | Approx. Total Dose | Number of Determinations | Mean Flux | S. D. |
|---|---|---|---|---|
| 1000 µg/ml | 1500 µg | 10 | 2.98 µg | 0.68 µg |
| 1500 µg/ml | 2250 µg | 10 | 4.75 µg | 1.19 µg |
| 2000 µg/ml | 3000 µg | 10 | 6.19 µg | 1.41 µg |
| 3000 µg/ml | 45000 µg | 10 | 6.84 µg | 1.49 µg |
| 4000 µg/ml | 6000 µg | 10 | 9.17 µg | 1.41 µg |
| 6000 µg/ml | 9000 µg | 11 | 11.34 µg | 2.12 µg |
| 8000 µg/ml | 12000 µg | 10 | 15.16 µg | 2.41 µg |

In each of these separate determinations, of course, the usual flush and control runs were done in advance as in all other studies.

In the single drop experiments, a total dose of about 2500 ug fluxed about 4 ug at 90 minutes into the lower aqueous analog chamber. With the Soflens, the same approximate dose fluxed about 15 ug. Now, in the constant flow 90 minute experiments to yield a flux of about 15 ug, a total pilocarpine hydrochloride dose of 11,000 to 12,000 ug was required, suggesting therefore that the constant flow system is in the order of one fourth as efficient as the lens system (115,000 vs. 2500). However, that the constant flow system is more efficient in turn than the single drop system is indicated by the finding that to produce a flux of 4 ug in 90 minutes, the constant flow system requires a total dose of something well under 2500 ug (perhaps 2000 to 2100 ug, by extrapolation).

EXAMPLE 4

Vehicle for Enhanced Non-Surgical Antibiotic Administration

Novel antibiotic ointments are made by dissolving in isotonic drug solution at ambient temperature 23% of the copolymer in Example 1. Dissolution is judged to be complete when there is obtained a solution free of any particulate matter on low power microscope examination.

The drug solution in this example is gentamycin sulfate reagent solution (Schering), 50 mg/ml. The drug concentration in the solution is adjusted so that the novel ointments can be prepared with final concentrations of gentamycin of 12.5 mg/m., 6.25 mg/ml, and 3.12 mg/ml., respectively. (The commercial preparation of this antibiotic for use as drops, Garramycin-Schering, contains 3 mg/ml, approximating the 3.12 mg/ml concentration of the novel ointment).

A culture of *Pseudomonas aeruginosa*, the most common cause of destructive endophthalmitis, is obtained from a human case. This culture is shown to be sensitive by in vitro tube dilution to less than 4 ug/ml of gentamycin sulfate. The culture is maintained at 4° C. on blood agar plates. The cultures are used for intravitreal innoculation in rabbits to produce a standard endophthalmitis. The dilution and bacteriological techniques employed are similar to those of D. R. May et al (Am. J. Ophth. 91:487, 1974, presented at Assoc. for Res. in Vis. and Ophth. Sarasota, April, 1972.). Intravitreal injection of 500 to 1000 viable *P. aeruginosa* organisms in 0.1 ml produces rapidly developing endophthalmitis of a highly virulent and destructive type.

Six hours after intravitreal injection of the bacterial suspension, gentamycin sulfate is applied to the eye in various ways. These include:

1. Untreated controls.
2. Treatment with hourly flooding of the conjunctival sac with standard commercial 0.3% Garramycin (gentamycin-Schering) together with intramuscular injection of 5 mg/kg/day gentamycin sulfate in 3 divided doses. The drop doses between midnight and 6 AM are omitted after the first 24 hours, but the protocol is otherwise continued for 5 days.
3. Eyes treated with subconjunctival injections of 10 mg gentamycin sulfate in 0.25 ml every 12 hours together with systemic medication as described in (2) above.
4. Eyes treated with various dilutions of gentamycin sulfate in the novel ointment with systemic gentamycin dosage as in (2) above. Ointment is administered every 6 hours.

5. Eyes treated with intravitreal injection of a solution of gentamycin sulfate containing 500 ug/0.1 ml in total intravitreal injected volume of 0.1 ml.

Results of these various modes of treatment with the same agent of a standard intravitreal *P. aeruginosa* infection would suggest that the most effective treatment method is intravitreal injection. In the treatment of human cases, however, this method has many drawbacks and hazards.

Those eyes treated with a combination of drops and systemic intramuscular injection would appear little different from the controls. In both situations, the eyes are destroyed and the vitreous reduced to a bag of purulent matter within 3 days.

Subconjunctival injection of the antibiotic combined with systemic intramuscular treatment appears to be considerably more effective. The speed of the infection is impeded and in a few cases, the eyes remain intact after 5 days, although still variably involved in the endophthal mitic reaction.

Eyes treated with the two stronger concentrations of gentamycin in the novel ointment together with systemic intramuscular gentamycin appear to fare at least as well as those subjected to subconjunctival injections.

Observations would suggest that the capability of the antibiotic agent to enter through the corneal barrier into the internal eye when used in the novel ointment in convenient and non-toxic concentration equals or possibly betters the effect of the more technically difficult and potentially hazardous subconjunctival injection technique. The novel ointment in this situation, in addition, has the marked advantage in that it may be repeated at any desired intervals without hazard, or discomfort and fear on the part of the patient which an intraocular injection entails.

In addition, the ease, comfort and patient acceptability of the novel ointment allows its use in other situations such as, for example, prophylactically before ocular surgery, especially in the presence of potentially complicating conditions such as chronic blepharitis. This use in prophylaxis would be far superior to use of drop therapy in the same situation, since in the case of the novel ointment sterilization may be effected not only in the conjunctival sac but in the internal eye as well.

EXAMPLE 5

Vehicle for Enhanced Intracorneal Antibiotic Administration

Reference is made in this Example to Example 4 above. The polymer of Example 2 was used in lieu of the polymer of Example 1. Enhanced penetration into the tissues of the internal eye of effective antibiotics for control of a highly virulent endophthalmitis condition has implications for the control of bacterial ulcers of the cornea itself.

Because the intact drug must penetrate the cornea to affect the tissues of the internal eye, the transcorneal flux enhancement in the novel ointment vehicle will be a useful agent in the treatment of septic lesions of the cornea itself. Preliminary studies show that in experimental corneal ulcers in rabbits induced by *Staphylococcus Aureus* ATCC 25923, Tobramycin (Lilly), gentamycin (Garromycin-Schering), and Cephaloridine (Loridine-Lilly) show significantly enhanced effects when used in conjunction with the novel ointment as a delivery method, relative to larger total doses used in simple drop therapy, however frequent.

EXAMPLE 6

Vehicle for Enhances Intra-ocular Antimetabolite Administration

Reference is made to Examples 3 and 4 above showing enhanced intra-ocular and corneal penetration of various drugs, including the anti-glaucoma agent, pilocarpine hydrochloride, and various antibiotic drugs when applied to the cornea in the novel ointment. The vehicle method also has significance for control of sterile inflammations of the uveal tract (anterior uveitis including iritis, iridocyclitis, and pars planitis). The agents which can be used within the novel ointment include the various soluble corticosteriods such as dexamethasone (Decadron, Merck, Sharpe and Dohme) as well as general antimetabolites such as indomethacin and oxyphenbutazone, and more specific antimetabolites such as iododeoxyuridine and cytosine arabinoside. Those conditions already shown to be therapeutically affected by these various agents in standard drop form will be expected to be more affected by the same agents introduced more efficiently into the anterior ocular segment by use of the novel ointment.

What is claimed is:

1. A viscous, homogeneous opthalmic formulation comprising
   1. water,
   2. a therapeutically effective amount of a medicament, and
   3. a solid, compatible, non-toxic polymer which is a water-soluble acrylic polymer, a water-soluble 2-alkenamide polymer or a water-soluble ethylenimine polymer, the concentration of said polymer being sufficient to impart to the formulation a slow-flowing characteristic which is substantially shape-retaining as said formulation is initially forced from a tube under mild hand squeezing of the tube.

2. The formulation of claim 1 wherein said water soluble polymer is (a) characterized by the recurring unit

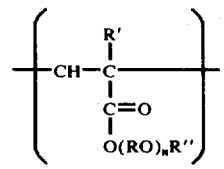

wherein R is a divalent aliphatic radical of 2 to 8 carbon atoms; wherein R' is hydrogen or alkyl of 1 to 4 carbon atoms; wherein R" is hydrogen or alkyl of 1 to 12 carbon atoms; and wherein $n$ is an integer of at least 1, (b) a water-soluble 2-alkenamide polymer, (c) a water-soluble ethylenimine polymer, or (d) a water-soluble sodium salt of sucrose acrylate polymer having free acid groups.

3. The formulation of claim 2 wherein the maximum concentration of the polymer is 35%.

4. The formulation of claim 2 wherein the upper limit on the viscosity is 50,000 cps.

5. The formulation of claim 2 wherein the upper limit on the viscosity is 25,000 cps.

6. The formulation of claim 2 consisting essentially of (1), (2) and (3).

7. The formulation of claim 1 wherein said polymer is a water soluble acrylic polymer.

8. The formulation of claim 2 wherein said polymer is characterized by the recurring unit

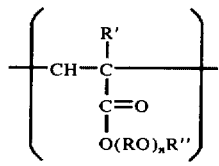

wherein R is a divalent aliphatic radical of 2 to 8 carbon atoms; wherein R' is hydrogen or alkyl of 1 to 4 carbon atoms; wherein R'' is hydrogen or alkyl of 1 to 12 carbon atoms; and wherein $n$ is an integer of at least 1.

9. The formulation of claim 8 wherein said polymer contains at least about 50 weight percent of said recurring unit.

10. The formulation of claim 8 wherein said polymer contains at least about 80 weight percent of said recurring unit.

11. The formulation of claim 9 wherein R is ethylene; wherein R' is methyl; wherein R'' is hydrogen; and wherein $n$ is one.

12. The formulation of claim 2 wherein said polymer is a water-soluble 2-alkenamide polymer.

13. The formulation of claim 2 wherein said polymer is a water soluble ethyleneimine polymer.

14. The formulation of claim 2 wherein said polymer is a water-soluble polymer of a hydroxy lower alkyl acrylate, of a hydroxy lower alkyl methacrylate, of a hydroxy lower alkoxy lower alkyl acrylate, or of a hydroxy lower alkoxy lower alkyl methacrylate, and of a non-toxic, water-soluble, polymer-forming comonomer which is present in sufficient amount that the copolymer is water soluble.

15. The formulation of claim 14 wherein the lower alkyl and lower alkoxy groups have 2 to 3 carbon atoms.

16. The formulation of claim 15 wherein the water-soluble polymer is a copolymer of hydroxyethyl acrylate, of hydroxypropyl acrylate, of hydroxyethyl methacrylate, or of hydroxypropyl methacrylate and of said comonomer.

17. The formulation of claim 8 wherein said polymer has an average-molecular weight of from about 25,000 to about 250,000.

18. The formulation of claim 2 wherein said medicament is pilocarpine in its pharmacologically acceptable salt.

19. The formulation of claim 18 wherein said polymer is a polymer of 2-hydroxyethyl methacrylate.

20. The method of applying to the external ocular tissues the formulation of claim 2 in an amount so that there is provided effective prolonged surface contact of said formulation with said external ocular tissues thereby allowing enhanced pulsing of medicament to the tissues in the internal eye.

21. The method of claim 20 wherein said formulation comprises pilocarpine in its pharmacologically acceptable salt and a polymer of 2-hydroxyethyl methacrylate.

22. The method of claim 21 wherein said formulation is slow-flowing viscous, homogeneous cream.

23. A viscous, homogeneous ophthalmic formulation comprising
 1. water
 2. a therapeutically effective amount of a medicament, and
 3. a solid, compatible, non-toxic polymer which is a water-soluble acrylic polymer, a water-soluble 2-alkenamide polymer or a water-soluble ethylenimine polymer, said polymer being dissolved in said water, said polymer being compatible with said medicament, said polymer being employed in an amount sufficient to provide a viscous formulation having a slow-flow characteristic.

24. The formulation of claim 23 wherein the medicament is a corticosteroid.

25. The formulation of claim 23 wherein the medicament is an antibiotic.

26. The formulation of claim 25 wherein the antibiotic is neomycin, bacitracin, a penicillin or a sulfonamide.

27. The formulation of claim 26 wherein the antibiotic is a soluble sulfonamide.

28. The formulation of claim 23 wherein the medicament is a pharmacologically acceptable salt of pilocarpine.

29. The method of applying to the external ocular tissues the formulation of claim 23 in an amount providing effective prolonged surface contact of said formulation with said external ocular tissues thereby allowing enhanced pulsing of medicament to the tissues in the internal eye.

30. The composition of claim 23 wherein the concentration of the polymer is up to 35% based on the total weight of the formulation.

31. The composition of claim 30 wherein the concentration of the polymer is 12 to 30% based on the total weight of the formulation.

32. The formulation of claim 30 wherein the concentration of the polymer is 12 to 35%.

33. The formulation of claim 32 consisting essentially of (1) water, (2) said medicament and (3) said polymer.

34. The formulation of claim 23 consisting essentially of (1) water, (2) said medicament and (3) said polymer.

* * * * *